United States Patent [19]

Lyons

[11] 3,987,112
[45] Oct. 19, 1976

[54] PROCESS FOR MANUFACTURE OF CATECHOL

[75] Inventor: James E. Lyons, Wallingford, Pa.

[73] Assignee: Sun Ventures, Inc., St. Davids, Pa.

[22] Filed: Oct. 17, 1974

[21] Appl. No.: 515,762

Related U.S. Application Data

[63] Continuation-in-part of Ser. Nos. 375,195, June 29, 1973, abandoned, Ser. No. 375,260, June 29, 1973, abandoned, Ser. No. 393,514, Aug. 31, 1973, abandoned, and Ser. No. 457,045, April 1, 1974.

[52] U.S. Cl. .......................... 260/621 H; 260/348.5 V; 260/348C; 260/348.5F; 260/631H; 260/666A

[51] Int. Cl.² ........................................... C07C 39/08

[58] Field of Search ............ 260/625, 621 H, 621 R, 260/348 R, 631 H, 621 F, 631 A, 348 C, 348.5 F, 666 A, 348.5

[56] References Cited
UNITED STATES PATENTS 2,599,089  6/1952  Castle et al. ................... 260/631 H 3,627,833  12/1971  Tobis ............................ 260/621 H Primary Examiner—James O. Thomas, Jr.
Assistant Examiner—W. B. Lone
Attorney, Agent, or Firm—J. Edward Hess; Donald R. Johnson; Stanford M. Back

[57] ABSTRACT

A 4-stage process for the production of catechol, starting with a mixture of cyclohexanol-cyclohexanone ("KA-oil"), is provided herein whereby the starting mixture is first hydrotreated to convert the cyclohexanone to cyclohexanol, the cyclohexanol dehydrated to form cyclohexene which, in turn, is oxidized to 1,2-epoxy-3-hydroxy-cyclohexane. Dehydrogenation of this latter compound yields catechol. Volatiles and residue from the second stage are advantageously recycled to the KA-oil feed stream, and $H_2$ from the last stage recycled to the hydrotreating step.

30 Claims, 1 Drawing Figure

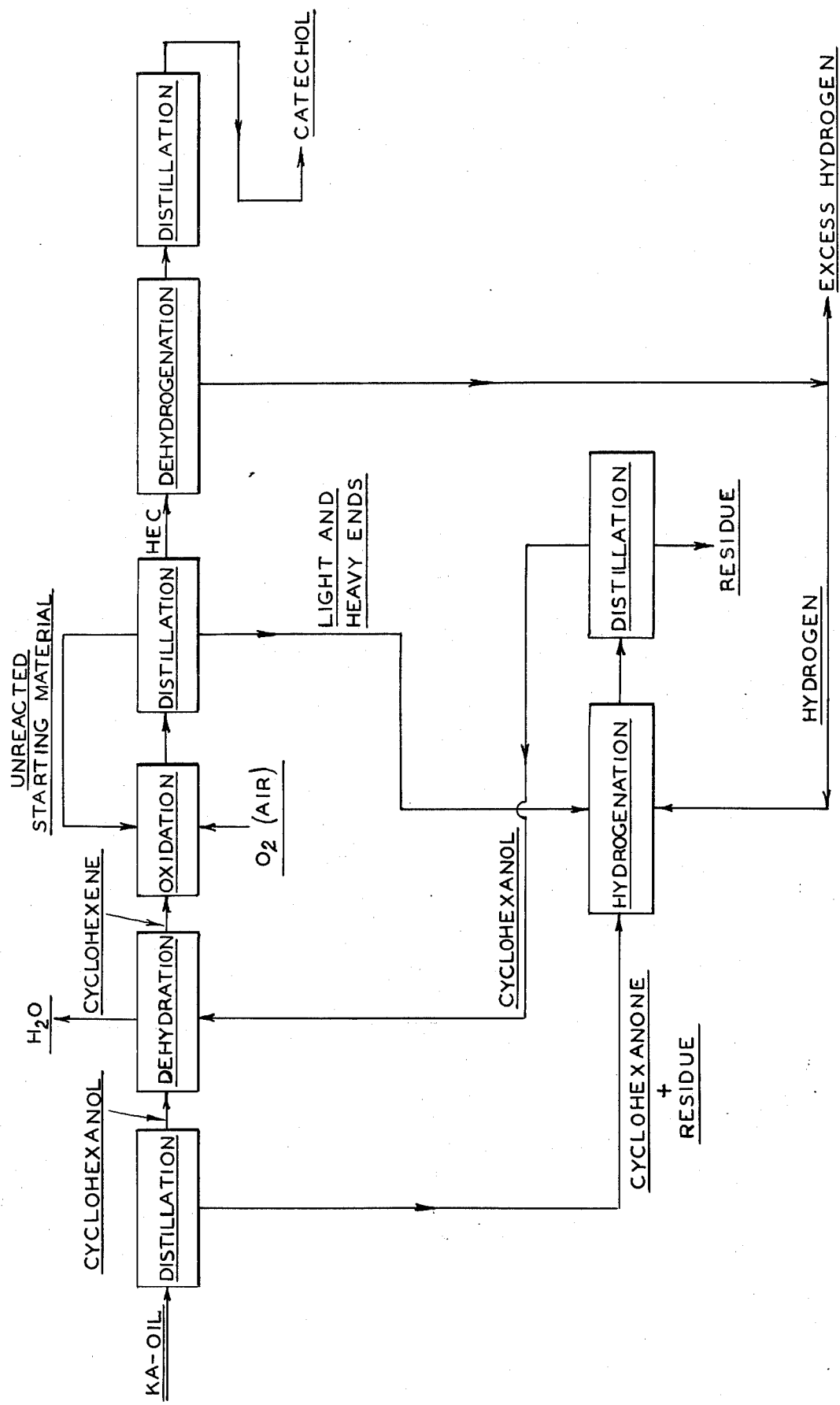

PROCESS FOR MANUFACTURE OF CATECHOL

CROSS-REFERENCE TO RELATED CASES

This application is a continuation-in-part of Ser. Nos. 375,195 now abandoned; 375,260 now abandoned; 393,514 now abandoned; and 457,045 filed by James E. Lyons on June 29 and Aug. 31, 1973, and Apr. 1, 1974, respectively.

BACKGROUND OF THE INVENTION

This invention relates to a process for the preparation of catechol. More particularly, this invention relates to a balanced, integrated, multi-step synthesis of catechol starting with a mixture of cyclohexanol and cyclohexanone.

Certain aspects of the invention are described in earlier-filed applications of James E. Lyons, listed above, details of which are set forth below.

DESCRIPTION OF THE DRAWING

FIG. 1 is a block flow diagram of a catechol plant utilizing the above-described process. Various recycle steps are shown which provide an integrated and economical conversion of the KA-oil.

SUMMARY OF THE INVENTION

In accordance with this invention, catechol is prepared in high yield from a mixture of cyclohexanol and cyclohexanone in accordance with the following overall reaction scheme:

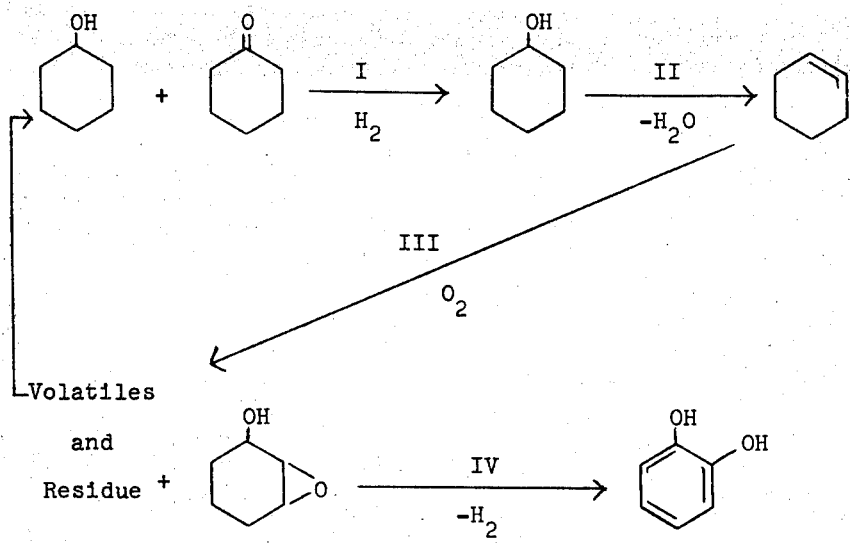

Thus, in summary, in the first step the cyclohexanone in the starting mixture is hydrotreated to convert it to cyclohexanol, followed by dehydration of the cyclohexanol to form cyclohexene. This latter material, is oxidized to 1,2-epoxy-3-hydroxycyclohexane (HEC), which is then dehydrogenated to yield catechol. Residues and volatile materials recovered from the epoxidation step are advantageously recycled to the starting feed, and $H_2$ from the last stage recycled to the first stage hydrogenation.

It will thus be appreciated from the foregoing description and drawing that the instant process represents a well-integrated and balanced method for obtaining catechol at an overall plant yield of up to about 90%, starting with a readily-available feedstock, wherein the hydrotreating step serves not only to hydrogenate the cyclohexanone in the starting feed, but also the light and heavy ends recovered from the oxidation step in order to provide additional cyclohexanol starting material. Moreover, the economics of this process is further enhanced by the ability of the dehydrogenation step to provide all of hydrogen supply necessary for the operation of said hydrotreater.

DESCRIPTION OF THE INVENTION

Step I

The preferred starting material for the present process is a commercially available preparation known as KA oil, which is conventionally used in the manufacture of such materials as caprolactam and adipic acid. The KA oil is actually a mixture of about 60–80% cyclohexanol, with the remainder comprising cyclohexanone. Since, in accordance with the process, it is important that the material be substantially converted to cyclohexanol before proceeding to the next step, the KA oil is first hydrotreated to convert the cyclohexanone component to cyclohhexanol.

This hydrogenation can readily be achieved in the presence of such hydrogenation catalysts as activated copper chromite, preferably on charcoal, typically at about 150° to 350°C, about 1500 psig $H_2$, and an LHSV of 1.0. The process is carried out in a continuous fashion in the liquid phase, using finely a divided catalyst bed. Instead of copper chromite, other hydrogenation catalysts such as rhodium or ruthenium on various supports may be employed if desired.

Alternatively, and more preferably, as shown in the accompanying flow diagram, the KA oil may first be distilled to separate the cyclohexanone from the cyclohexanol, followed by the above-described hydrogenation of just the cyclohexanone. Distillation of the resulting product mixture provides additional cyclohexanol to be combined with the original cyclohexanol for the next step of the process, plus certain residues. This distillation of the product cyclohexanol is readily achieved at 161°C at atmospheric pressure.

Step II

The second stage of the process comprises the conversion of cyclohexanol to cyclohexene. This is accomplished by dehydration, employing any one of many known dehydration catalysts, including activated aluminas such as gamma—or etaalumina, thoria, synthetic silica-aluminas, crystalline zeolites, acid-treated clays and the like, of which gamma alumina is preferred. The reaction is conveniently achieved by passing the cyclohexanol over a fixed bed of the activated alumina in the vapor phase at temperatures in the range of about 200° to 400°C., preferably about 300° to 350°C., at a volume rate of about 1, and recovering the resulting cyclohexene.

Step III

The third stage of the catechol preparation comprises the oxidation of cyclohexene to form 1,2-epoxy-3-hydroxycyclohexane (HEC). This oxidation may readily be achieved in accordance with the teachings of earlier-filed copending application U.S. Ser. No. 375,195 filed June 29, 1973, or U.S. Ser. No. 393,514, filed Aug. 31, 1973, both in the name of James E. Lyons. As taught in U.S. Ser. No. 375,195, cyclohexene may be oxidized to 1,2-epoxy-3-hydroxycyclohexane (HEC) by contacting the cyclohexene with air or oxygen in the presence of a catalyst comprising an ion-exchanged bimetallic catalyst wherein one of said metals is from Group IB or Group VIII of the Periodic Table, and the other is from Group VB. Thus, for example, a preferred catalyst would be a cobalt (or copper) and vanadium-exchanged x-zeolite.

Alternatively, as disclosed in Ser. No. 393,514, (above), a vanadium catalyst of the formula $$L_x V^n X_y$$

may be employed in a like process, wherein L is a neutral ligand; X is an anionic ligand; $x$ is an integer of from 0–6; $y$ is an integer of from 0–2 and is equal to $n$, but when $n$ is 0, then $x$ equals at least 1; and $n$ denotes the valance of vanadium and is an integer of from 0–2. Included amongst these catalysts are such compounds as $C_6H_5V(CO)_4$, $V(CO)_6$; and the like.

These reactions are generally carried out in the liquid phase at temperatures in the range of from about 25° to 150°–200°C for periods of from about 1 to 10–20 hours. The oxygen flow rate will depend upon the reactor size, and can readily be determined by a skilled operator.

The reaction product from this oxidation step consists of a mixture of about 70% unreacted cyclohexene and 30% product material. The unreacted cyclohexene represents the first cut in the distillation of the reaction mixture and is recycled to the oxidizer unit as shown in the flow diagram. The relative amounts of oxidation products in the product material are: (1) volatile oxidation products: cyclohexen oxide, 2-cyclohexene-1-ol and 2-cyclohexene-1-one totalling 35–40% of the product material. These products distill as a second cut and are recycled to the hydrotreater to be converted to cyclohexanol as shown in the flow diagram; (2) 1,2-epoxy-3-hydroxycyclohexane totalling 50–60% of the product material. This is distilled as a third cut in the fractionation column; and (3) a non-volatile residue totalling 5–10% of the product material. These heavy ends comprise various dimers and polymers of oxidized olefin.

Distillation of the reaction mixture may be carried out at 10 mm, at which pressure the volatiles (unreached cyclohexene, 2-cyclohexene-1-one, 2-cyclohexene-1-ol and cyclohexene epoxide) distill prior to 90°C and pure 1,2-epoxy-3-hydroxycyclohexene (HEC) distills from 98° to 102°C. Pressures higher than 10 mm are also suitable but correspondingly higher boiling points result. Boiling in excess of 200° causes some product deterioration.

Step IV

In the final stage, the 1,2-epoxy-3-hydroxycyclohexane can be dehydrogenated in a manner disclosed in U.S. Ser. No. 457,045, filed Apr. 1, 1974 in the name of James E. Lyons, to form catechol. As taught therein, 1,2-epoxy-3-hydroxycyclohexane is contacted with a Group VIII transition metal dehydrogenation catalyst such as palladium, platinum, or ruthenium in the form of Pd-or Pt black, or on an inert support such as alumina, carbon kieselguhr or the like. This may be carried out in either the liquid or vapor phase. When the liquid phase is employed, the reaction is desirably carried out at temperatures of from about 175° to 350°C using high boiling alkyl or aralkyl hydrocarbon solvents such as phenyldodecane or dodecane. The catalyst should be present in amounts of from about 1 to 10 weight percent based on the weight of the starting material.

Alternatively, the dehydrogenation may be conducted in the vapor phase by passing the epoxyol down a tube or other suitable reactor filled with an inert refractory material such as Corhart (Corhart Industries) at a temperature of from about 250° to 400°C at a weight hourly space velocity of from about 0.1 to 10.0.

The reaction products are then recovered and separated, with the hydrogen generated being recycled to the afore-described hydrogenation step, as shown in the accompanying diagram. The product is then distilled and the catechol recovered.

EXAMPLE 1

Hydrogenation Unit

The starting material for this 4-stage process, KA oil, is a 70:30 by weight mixture of cyclohexanol and cyclohexanone. In order to convert the cyclohexanone portion to cyclohexanol, KA Oil is passed through a hydrotreater at 165°C, 1500 psig and LHSV of 1.0. The successful hydrogenation of this mixture of cyclohexanol and cyclohexanone is carried out under these conditions in a flow reactor over an activated copper chromite catalyst on charcoal to give a product which is 98–99% pure cyclohexanol.

The hydrotreater is also capable at varying time intervals of receiving light ends from the oxidizer (Example 3) and converting them to cyclohexanol in high yield. The light ends from the oxidizer are mostly 2-cyclohexene-1-ol, 2-cyclohexene-1-one and cyclohexene oxide (Example 3). The successful hydrogenation of a mixture of light ends containing 61% cyclohexene-1-one, 26% cyclohexene-1-ol and 11% cyclohexene oxide is carried out at 170°C under 1500 psig, LHSV 1.0 in a flow reactor over activated copper chromite on charcoal. Cyclohexanol is formed in 94% yield and can be recycled for dehydration.

If the heavy ends from the oxidizer are also charged to the hydrotreater, more cyclohexanol may be recovered for recycle. If heavy ends boiling below 300°C are passed through the hydrotreater at 200°C 1750 psig $H_2$, LHSV 1.0, a 28% yield of recoverable cyclohexanol results. The residue from this hydrotreatment is then discarded or used as fuel.

EXAMPLE 2

Dehydration Unit

Cyclohexene for the oxidation unit is manufactured by passing the cyclohexanol from the hydrotreater through a dehydration reactor. This step is carried out by passing cyclohexanol in the vapor phase through a flow reactor packed with active $\gamma 8$-$Al_2O_3$ at 350°C at a volume rate of 0.5 $sec^{-1}$. Cyclohexanol is converted in >99.5% to cyclohexene. Using $2B_2O_3 \cdot 3Al_2O_3$, high yields of olefin are also obtained.

EXAMPLE 3

Oxidizer Unit

Air, 3 atm., or oxygen 1.1 atms, is circulated through a liquid phase reactor charged with a 0.04% by weight solution of $[C_5H_5V(CO)_4]$ in cyclohexene. After a 4 hour residence time at 75°C. the contents of the reactor contain 70–75% unreacted cyclohexene, 25–30% product material of which about 55% is 1,2-epoxy-3-hydroxycyclohexane, 39% is light ends, and 6% heavy ends (residue distilling over 110°C at 10 mm).

EXAMPLE 4

Dehydrogenation Unit 1,2-epoxy-3-hydroxycyclohexane is dehydrogenated in a liquid phase continuous slurry reactor at 200°C over 10% palladium on carbon. A low partial pressure of hydrogen is maintained by sweeping with an inert (nitrogen) carrier gas. The substrate/solvent/catalyst ratio is 5/10/1 in the reactor.

The invention claimed is:
1. A process for the preparation of catechol which comprises the steps of:
   a. hydrotreating at 150°–350°C and in the presence of a hydrogenation catalyst a feed stream comprising cyclohexanone and cyclohexanol to convert said cyclohexanone to cyclohexanol;
   b. dehydrating said cyclohexanol in the presence of a dehydration catalyst at 200°–400°C to form cyclohexene;
   c. oxidizing said cyclohexene in the presence of a catalyst selected from the group consisting of (1) an ion-exchanged bimetallic catalyst wherein one of said metals is from Group IB or Group VIII of the Periodic Table, and the other is from Group VB, and (2) a vanadium catalyst of the formula

$LxV^nXy$ wherein L is a neutral ligand; X is an anionic ligand; x is an integer of from 0–6; y is an integer of from 0–2, and is equal to n, but when n is 0, then x equals at least 1, and n indicates the valence of vanadium and is an integer of from 0–2, at about 25°–150°C for about 1–20 hours to form 1,2-epoxy-3-hydroxycyclohexane; and
   d. dehydrogenating said 1,2-epoxy-3-hydroxycyclohexane in the presence of a dehydrogenation catalyst in the liquid phase at 175°–350°C in the presence of a high-boiling solvent to yield catechol and hydrogen.

2. The process according to claim 1 wherein the feed stream is first separated into cyclohexanol and cyclohexanone, the latter hydrogenated to form additional cyclohexanol, and the additional cyclohexanol passed directly to the dehydration step.

3. The process according to claim 1 wherein the bimetallic catalyst is a copper-or cobalt-, and vanadium-exchanged x-zeolite.

4. The process according to claim 1 wherein the vanadium catalyst is $C_6H_5V(CO)_4$.

5. The process according to claim 1 wherein the dehydrogenation of the 1,2-epoxy-3-hydroxycyclohexane is carried out in the presence of a Group VIII transition metal catalyst.

6. The process according to claim 5 wherein the Group VIII metal is palladium, platinum, ruthenium, osmium, iridium, or rhodium.

7. The process according to claim 6 wherein the metal is supported on alumina, carbon, kieselguhr, or graphite.

8. The process according to claim 1 wherein the hydrogen from the dehydrogenation step is recycled to the hydrotreating step.

9. A process for the preparation of catechol from cyclohexene which comprises the steps of:
   a. oxidizing cyclohexene in the presence of a catalyst selected from the group consisting of (1) an ion-exchanged bimetallic catalyst wherein one of said metals is from Group IB or Group VIII of the Periodic Table, and the other is from Group VB, and (2) a vanadium catalyst of the formula $LxV^nXy$ wherein L is a neutral ligand; X is an anionic ligand; x is an integer of from 0–6; y is an integer of from 0–2, and is equal to n, but when n is 0, then x equals at least 1, and n indicates the valence of vanadium and is an integer of from 0–2, at about 25°–150°C for about 1–20 hours to form 1,2-epoxy-3-hydroxycyclohexane; and
   b. dehydrogenating said 1,2-epoxy-3-hydroxycyclohexane in the presence of a dehydrogenation catalyst in the liquid phase at 175°–350°C in the presence of a high-boiling solvent to yield catechol and hydrogen.

10. The process according to claim 9 wherein the bimetallic catalyst is a copper-or cobalt-, and vanadium- exchanged x-zeolite.

11. The process according to claim 9 wherein the vanadium catalyst is $C_5H_5V(CO)_4$.

12. The process according to claim 9 wherein the dehydrogenation of the 1,2-epoxy-3-hydroxycyclohexane is carried out in the presence of a Group VIII transition metal catalyst.

13. The process according to claim 12 wherein the Group VIII metal is palladium, platinum, ruthenium, osmium, iridium, or rhodium.

14. The process according to claim 13 wherein the metal is supported on alumina, carbon, kieselguhr, or graphite.

15. The process according to claim 9 wherein the hydrogen from the dehydrogenation step is recycled to the hydrotreating step.

16. A process for the preparation of catechol which comprises the steps of:

a. hydrotreating at 150°–350°C and in the presence of a hydrogenation catalyst a feed stream comprising cyclohexanone and cyclohexanol to convert said cyclohexanone to cyclohexanol;
b. dehydrating said cyclohexanol in the presence of a dehydration catalyst at 200°–400°C to form cyclohexene;
c. oxidizing said cyclohexene in the presence of a catalyst selected from the group consisting of (1) an ion-exchanged bimetallic catalyst wherein one of said metals is from Group IB or Group VIII of the Periodic Table, and the other is from Group VB, and (2) a vanadium catalyst of the formula.

$$L_xV^nX_y$$

wherein L is a neutral ligand; X is an anionic ligand; $x$ is an integer of from 0–6; $y$ is an integer of from 0–2, and is equal to $n$, but when $n$ is 0, then $x$ equals at least 1, and $n$ indicates the valence of vanadium and is an integer of from 0–2, at about 25°–150°C for about 1–20 hours to form 1,2-epoxy-3-hydroxycyclohexane; and d. dehydrogenating said 1,2-epoxy-3-hydroxycyclohexane in the presence of a dehydrogenation catalyst in the vapor phase at about 250°–400°C at a LHSV of about 0.1–10.0, to yield catechol and hydrogen.

17. The process according to claim 16 wherein the feed stream is first separated into cyclohexanol and cyclohexanone, the latter hydrogenated to form additional cyclohexanol, and the additional cyclohexanol passed directly to the dehydration step.

18. The process according to claim 16 wherein the bimetallic catalyst is a copper- or cobalt-, and vanadium-exchanged x-zeolite.

19. The process according to claim 16 wherein the vanadium catalyst is $C_6H_5V(CO)_4$.

20. The process according to claim 16 wherein the dehydrogenation of the 1,2-epoxy-3-hydroxycyclohexane is carried out in the presence of a Group VIII transition metal catalyst.

21. The process according to claim 20 wherein the Group VIII metal is palladium, platinum, ruthenium, osmium, iridium or rhodium.

22. The process according to claim 21 wherein the metal is supported on alumina, carbon, kieselguhr or graphite.

23. The process according to claim 16 wherein the hydrogen from the dehydrogenation step is recycled to the hydrotreating step.

24. A process for the preparation of catechol from cyclohexene which comprises the steps of:
a. oxidizing cyclohexene in the presence of a catalyst selected from the group consisting of (1) an ion-exchanged bimetallic catalyst wherein one of said metals is from Group IB or Group VIII of the Periodic Table, and the other is from Group VB, and (2) a vanadium catalyst of the formula $$L_xV^nX_y$$

wherein L is a neutral ligand; X is an anionic ligand; $x$ is an integer of from 0–6; $y$ is an integer of from 0–2, and is equal to $n$, but when $n$ is 0, then $x$ equals at least 1, and $n$ indicates the valence of vanadium and is an integer of from 0–2, at about 25°–150°C for about 1–20 hours to form 1,2-epoxy-3-hydroxychyclohexane; and b. dehydrogenating said 1,2-epoxy-3-hydroxycyclohexane in the presence of a dehydrogenation catalyst in the vapor phase at about 250°–400°C at a LHSV of about 0.1–10.0, to yield catechol and hydrogen.

25. The process according to claim 24 wherein the bimetallic catalyst is a copper- or cobalt-, and vanadium-exchanged x-zeolite.

26. The process according to claim 24 wherein the vanadium catalyst is $C_5H_5V(CO)_4$.

27. The process according to claim 24 wherein the dehydrogenation of the 1,2-epoxy-3-hydroxycyclohexane is carried out in the presence of a Group VIII transition metal catalyst.

28. The process according to claim 27 wherein the Group VIII metal is palladium, platinum, ruthenium, osmium, iridium or rhodium.

29. The process according to claim 28 wherein the metal is supported on alumina, carbon, kieselguhr or graphite.

30. The process according to claim 24 wherein the hydrogen from the dehydrogenation step is recycled to the hydrotreating step.

* * * * *